United States Patent [19]

Marbach

[11] 4,054,488
[45] Oct. 18, 1977

[54] PRESERVATION OF GLUCOSE IN BLOOD SAMPLES

[76] Inventor: Edward P. Marbach, 4607 Marwood Drive, Los Angeles, Calif. 90065

[21] Appl. No.: 661,625

[22] Filed: Feb. 26, 1976

Related U.S. Application Data

[63] Continuation-in-part of Ser. No. 604,551, Aug. 14, 1975, abandoned.

[51] Int. Cl.$^2$ ............................................. G01N 33/16
[52] U.S. Cl. .......................................... 195/1.8; 21/58; 23/230 B; 252/408
[58] Field of Search ................. 23/230 B; 21/2, 58; 252/408; 195/1.8

[56] References Cited

U.S. PATENT DOCUMENTS

| | | | |
|---|---|---|---|
| 3,629,142 | 12/1971 | Marbach | 23/230 B X |
| 3,682,835 | 8/1972 | Louderback | 23/230 B X |
| 3,847,738 | 11/1974 | Brake | 195/1.8 |
| 3,859,049 | 1/1975 | Ware | 23/230 B |
| 3,873,467 | 3/1975 | Hunt | 23/230 B X |
| 3,874,384 | 4/1975 | Deindoerfer | 195/1.8 X |

OTHER PUBLICATIONS

White et al, *Principles of Biochemistry,* 4th Ed., 238–239, 398–399, McGraw-Hill, N. Y. (1968).
Chemical Abstracts, 78:157266z (1973).
Chemical Abstracts, 75:107198w (1971).
Chemical Abstracts, 70:56189f (1969).
Chemical Abstracts, 62:1222d (1965).

*Primary Examiner*—Sidney Marantz
*Attorney, Agent, or Firm*—Keith D. Beecher

[57] ABSTRACT

A process and preservatives for preventing glycolysis in blood samples so as to preserve the glucose content and lactic acid content thereof. The preservatives do not produce any significant hemolysis in the blood sample, and they do not interfere with any of the known blood constituents. The preservatives comprise salts of Iodoacetic acid, such as Tris-Iodoacetate [$(CH_2OH)_3NH_3$.$CO_2 - CH_2I$]; salts of Bromoacetic acid, such as Tris-Bromoacetate [$(CH_2OH)_3NH_3CO_2 - CH_2Br$], or Sodium Bromoacetate [$NaO_2CCH_2Br$]; and salts of mono Chloroacetic acid ($ClCH_2COOH$), such as Sodium Chloroacetate ($NaO_2CCH_2Cl$).

10 Claims, No Drawings

PRESERVATION OF GLUCOSE IN BLOOD SAMPLES

BACKGROUND OF THE INVENTION

It is the usual practice in modern hospitals to perform a variety of chemical and other tests on whole blood samples obtained from the patients. One important test is to determine the glucose content in the whole blood sample. However, due to glycolysis, the whole blood sample rapidly loses its glucose content under normal ambient conditions, unless some preservative is included in the sample to prevent glycolysis. However, it is important that the preservative does not produce any significant hemolysis in the sample which would tend to destroy its effectiveness. Also, it is important that the preservative does not affect other blood constituents so as to interfere with the results of other tests that are to be performed on the blood sample.

Sodium fluoride has been extensively used in the past as a preservative for glucose in blood samples. Sodium fluoride does prevent glycolysis, but it is known to interfere with certain enzyme reactions, such as urease. Also, glucose results have been found to be affected by sodium fluoride when certain oxidaseperoxidase techniques are employed.

Sodium iodoacetate has also been used in the past to prevent the loss of glucose in blood samples (see, for example, Principles of Biochemistry, 4th Edition, McGraw-Hill (1968) Pages 238, 239 and 398, 399). This latter preservative is preferable to sodium fluoride since it has the advantage of not interfering with the urease reaction when determining urea nitrogen. However, both the sodium fluoride and sodium iodoacetate preservatives have a disadvantage in that they produce excessive hemolysis in the blood sample.

The principal objective of the present invention is to provide preservatives for preventing glycolysis in the blood samples, which have all the advantages of sodium iodoacetate in that they do not interfere in any way with any of the other known blood constituents, and which have the additional advantage over sodium iodoacetate that they do not produce any significant hemolysis in the blood samples or add sodium to the sample.

The preservatives of the present invention have been found to stabilize glucose in a blood sample for at least twenty-four hours when standing on the clot at room temperature. The preservatives constituting the preferred embodiments of the invention are Tris-Iodoacetate; either Sodium or Tris Bromoacetate, or salts of mono Chloroacetic acid. The Tris-Iodoacetate preservative at 0.4 mg/ml of blood has been found to produce four and one-half times less hemolysis than fluoride. The Sodium Bromoacetate at 1 mg/ml of blood has been found to produce no hemolysis. Chloroacetic acid salts have been found to exhibit the same glycolytic properties as the Iodo and Bromo Acetic acid salts. Other salts of Iodoacetic acid, such as ammonium and other amines, are also effective for the purpose.

DETAILED DESCRIPTION OF THE PREFERRED EMBODIMENTS

I. Formulation of Tris-Iodoacetate.

Dissolve 9 g iodoacetic acid (Eastman Kodak Company) in 15 ml of $H_2O$. Heat and stir gently to about 37° to 40° C and add slowly 6 gms of Trisma Base (Sigma Chemical Company). When all is dissolved the pH is about 7. Allow to cool in refrigerator. Filter and wash crystals which form with about 2 to 3 ml of $H_2O$. Dry at room temperature.

II. Formulation of Tris Bromoacetate.

Dissolve 6.7 grams of Bromoacetic acid (Eastman) in 10 ml distilled water. Heat and stir gently to 45°–50° C, add 6.3 grams Tris (Trisma Base, Sigma). When all is dissolved the pH is about 6.8. Allow to cool in freezer for about ½ hour. Filter and white crystals and wash with 5–10 ml $H_2O$. Dry at 56° C for 4–5 hours.

III. Formulation of Sodium Bromoacetate

½ gram Bromoacetic acid is dissolved in one ml of water and 1 ml of 3.6N NaOH is added.

To use, add 0.030 ml of this solution to 10 ml of whole blood to produce a concentration of 1 mg of sodium bromoacetate per ml of blood.

A test comparison of the effectiveness of tris-iodoacetate and sodium bromoacetate as compared with the sodium fluoride and sodium iodoacetate preservatives of the prior art is revealed by the following table.

TABLE I

| Preservative | Amount (mg/ml) | Hemolysis plasma hemoglobin mg/100 ml | Percentage loss of glucose after standing on cell 24 hrs. at room temperature |
|---|---|---|---|
| None (control | | 5 | 29% |
| Na Fluoride (Prior art) | 2.5 | 55 | 3.8% |
| Tris Iodoacetate | 3.0 | | <1% |
| Tris Iodoacetate | 0.8 | 23 | <1% |
| Tris Iodoacetate | 0.4 | 16 | <2% |
| Tris Iodoacetate | 0.2 | 13 | 1% |
| Na Iodoacetate (Prior art) | 2.0 | 61 | 2.8% |
| Na Iodoacetate (Prior art) | 0.5 | 18 | 3.1% |
| Na Bromoacetate | 1.0 | 3 | 1% |

SUMMARY

The Iodoacetate, Chloroacetate and Bromoacetate salts prevent loss of glucose (glycolysis) as effectively as or better than fluoride. The Tris-Iodoacetate produces less hemolysis than the sodium salt. The bromoacetate salt produces less hemolysis than the iodoacetate salt. Only the sodium salt of Iodoacetate at 2 mg/ml produces more hemolysis than fluoride.

Tris-Iodoacetate was tested at 3 mg/ml of blood and tris-bromoacetate at 2.5 mg/ml. These concentrations are equimolar to 2 mg of Sodium Iodoacetate that is each contains 9.8 millimoles/liter. Both of these have essentially no hemolysis while the Sodium Iodoacetate at 2 mg/ml had heavy hemolysis. Therefore, the upper range can be extended to substantially 30 mg/ml.

The test results of Tris-Iodoacetate are evidenced by the following Table 2.

TABLE 2

| Additive | Amount (mg/ml) | Hemolysis plasma hemoglobin mg/100 ml | Percentage loss of glucose after standing on cell 24 hours at room temperature |
|---|---|---|---|
| K EDTA | 1.5 | 2 | 98% |
| KEDTA + Tris-Iodoacetate | 0.3 | 13 | 11% |

| HEMATOLOGY | Additives | |
|---|---|---|
| Test | EDTA | EDTA + Tris-Iodoacetate |
| White blood count | 8.1 | 8.1 |
| Red Blood Count | 4.89 | 4.90 |
| Hemoglobin gm/dl | 15.1 | 15.2 |
| MCV | 89 | 90 |
| MCH | 30.7 | 30.7 |
| MCHC | 34.2 | 34.6 |

SUMMARY

Tris-Iodoacetate when added to a CBC tube (EDTA) prevents loss of glucose while not interfering with hematological test. Therefore, Tris-Iodoacetate, Tris Bromoacetate and either Tris or Sodium Bromoacetate can be added to other additives which prevent clotting such as Heparin, EDTA and oxalate and not interfere with any of the test performed; while at the same time preventing the loss of glucose.

IV. Formulation of Sodium Chloroacetate.
Weight out 1.5 grams Chloroacetic Acid.
Add 8.4 ml distilled water.
Add 1.6 ml 10 N NaOH.

To use, add 0.10 ml of the solution to 10 ml of whole blood. This equals of concentration of 1.5 milligrams of sodium chloroacetate per milliliter of whole blood.

The test results of Sodium chloroacetate are as follows:

TABLE 3

|  | Tube # 1 $ClCH_2COONa$ 1 hr. | Tube # 2 $ClCH_2COONa$ 24 hr | Tube # 3 Fluoride 1 hr | Tube # 4 Fluoride 24 hr | Tube # 5 No Preservatives 1 hr | Tube # 6 No Preservatives 24 hr |
|---|---|---|---|---|---|---|
| Calcium | 8.9 | 9.2 | 4.2 | 1.8 | 9.2 | 9.7 |
| Phosphorus | 3.8 | 5.9 | 2.9 | 4.1 | 3.9 | 5.8 |
| Uric Acid | 3.0 | 3.0 | 2.8 | 2.9 | 3.1 | 3.0 |
| Cholesterol | 178 | 183 | 167 | 172 | 190 | 205 |
| Glucose | 79 | 75 | 79 | 81 | 80 | 46 |
| BUN | 15 | 15 | 15 | 15 | 15 | 15 |
| T. Bilirubin | 0.5 | 0.5 | 0.5 | 0.5 | 0.5 | 0.5 |
| T. Protein | 7.1 | 7.2 | 6.7 | 6.7 | 7.5 | 7.6 |
| Albumin | 4.5 | 4.5 | 4.1 | 4.3 | 4.8 | 4.9 |
| Alk P'tase | 72 | 73 | 60 | 51 | 76 | 79 |
| LDH | 109 | 111 | 340 | 384 | 115 | 135 |
| SGOT | 8 | 8 | 14 | 16 | 9 | 8 |

The aforesaid preservatives are placed in a test tube into which the whole blood sample is to be drawn, so that the final concentration of preservative is preferably of the order of 0.1–3 mg/ml of blood.

In a particular test, Tris-Iodoacetate was used in a blood sample at a concentration of 3mg/ml to blood. The following results were obtained:

TABLE 4

| CONSTITUENT | SERUM CONTROL | TRIS-IODOACETATE 1 HOUR | TRIS-IODOACETATE 24 HOURS |
|---|---|---|---|
| Calcium mg/dl | 9.4 | 9.3 | 9.1 |
| $PO_4$ mg/dl | 3.2 | 3.2 | 4.0 |
| Uric Acid mg/dl | 8.2 | 8.2 | 8.2 |
| Cholesterol mg/dl | 245 | 241 | 201 |
| Glucose mg/dl | 93 | 105 | 106 |
| BUN mg/dl | 16 | 16 | 16 |
| T. Bilirubin mg/dl | 1.1 | 1.1 | 1.0 |
| T. Protein g/dl | 7.3 | 7.3 | 7.2 |
| Albumin | 4.4 | 4.2 | 4.1 |
| Alk. Phosphatase IU | 42 | 40 | 41 |
| LDH IU | 162 | 151 | 154 |
| SGOT IU | 24 | 22 | 23 |
| SGPT IU | 29 | 20 | 29 |
| Creatinine mg/dl | 1.1 | 1.2 | 1.2 |
| Na meq/l | 142 | 138 | 138 |
| K meq/l | 3.9 | 4.5 | 6.8 |
| Chloride meq/l | 105 | 109 | 107 |
| $CO_2$ Content meq/l | 23 | 22 | 21 |

It will be readily apparent to those skilled in the particular art under consideration that other examples of the invention described herein may be devised from an understanding of the foregoing specification without departing from the spirit and scope of the invention. It is intended in the following claims to cover all such modifications, variations and adaptations which properly fall within the scope of the invention.

What is claimed is:

1. A preserved sample including whole blood and a preservative to preserve the glucose content of said whole blood, said preservative being selected from a group consisting of Tris-Iodoacetate, a salt of Bromoacetic acid or a salt of Chloroacetic acid.

2. The preserved sample defined in claim 1, in which the preservative is Tris-Iodoacetate in a concentration of substantially 3 milligrams per milliliter of whole blood.

3. The preserved sample defined in claim 1, in which said preservative is selected from a group consisting of Tris-Bromoacetate Sodium Bromoacetate or Sodium Chloroacetate.

4. The preserved sample defined in claim 3, in which the concentration of the preservative in the whole blood is substantially a range of 0.1–3 milligrams of preservative per milliliter of whole blood.

5. The preserved sample defined in claim 3, in which the preservative is selected from a group consisting of Sodium Bromoacetate or Sodium Chloroacetate in a concentration of substantially 1.5 milligrams per milliliter of whole blood.

6. A process for preventing glycolysis in a whole blood sample which comprises adding a preservative selected from a group consisting of Tris-Iodoacetate, a salt of Bromoacetic acid or a salt of Chloroacetic acid to the whole blood sample.

7. The process defined in claim 6, in which the preservative is Tris-Iodoacetate in a concentration of substantially 3 milligrams per milliliter of whole blood.

8. A process for preventing glycolysis in a whole blood sample which comprises adding a preservative selected from a group consisting of Tris-Bromoacetate Sodium Chloroacetate or Sodium Bromoacetate to the whole blood sample.

9. The process defined in claim 8, in which the concentration of the preservative in the whole blood sample is substantially in the range of 0.1–3 milligrams of preservative per milliliter of whole blood.

10. The process defined in claim 8, in which the preservative is Sodium Chloroacetate in a concentration of substantially 1.5 milligrams per milliliter of whole blood.

* * * * *